United States Patent
Andersson et al.

(10) Patent No.: US 9,308,138 B2
(45) Date of Patent: Apr. 12, 2016

(54) ABSORBENT ARTICLE HAVING INTAKE STRUCTURE

(75) Inventors: Patrik Andersson, Billdal (SE); Malin Lundman, Molnlycke (SE); Per Bergstrom, Gothenburg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/129,401

(22) PCT Filed: Jun. 28, 2011

(86) PCT No.: PCT/SE2011/050859
§ 371 (c)(1),
(2), (4) Date: Dec. 26, 2013

(87) PCT Pub. No.: WO2013/002686
PCT Pub. Date: Jan. 3, 2013

(65) Prior Publication Data
US 2014/0128828 A1    May 8, 2014

(51) Int. Cl.
*A61F 13/15*    (2006.01)
*A61F 13/20*    (2006.01)
(Continued)

(52) U.S. Cl.
CPC ..... *A61F 13/53717* (2013.01); *A61F 13/53752* (2013.01); *A61F 13/53756* (2013.01); *A61F 2013/53782* (2013.01); *A61F 2013/530875* (2013.01)

(58) Field of Classification Search
CPC ............. A61F 13/512; A61F 13/5146; A61F 13/53717; A61F 13/53743; A61F 2013/51355; A61F 2013/53782; A61F 13/494; A61F 13/5116; A61F 13/51305; A61F 13/51401; A61F 13/51478; A61F 13/53; A61F 2013/53076; A61F 2013/530861

USPC .............. 604/367, 378–384, 385.01, 385.101
See application file for complete search history.

(56) References Cited

U.S. PATENT DOCUMENTS 4,988,344 A    1/1991 Reising et al.
4,988,345 A *  1/1991 Reising .......................... 604/378
(Continued)

FOREIGN PATENT DOCUMENTS

EP    0316771 A2    5/1989
EP    0336578 A1    10/1989
(Continued)

OTHER PUBLICATIONS

Notification of First Office Action issued Nov. 28, 2014 in Chinese Patent Application No. 201180071909.0 (7 pages) with English Translation (7 pages).

(Continued)

*Primary Examiner* — Michele M Kidwell
(74) *Attorney, Agent, or Firm* — Drinker Biddle & Reath LLP

(57) ABSTRACT

An absorbent article including a fluid permeable topsheet, a fluid impermeable backsheet and an absorbent core enclosed between the topsheet and the backsheet. The absorbent core includes a first absorbent layer having an opening extending therethrough. A fluid flow control structure is arranged between the first absorbent layer and the backsheet. The fluid flow control structure is a layered structure including a non-perforated fibrous polymeric layer and a first perforated polymeric layer having a basis weight of from 50 g/m² to 100 g/m².

25 Claims, 3 Drawing Sheets

(51) Int. Cl.
*A61F 13/537* (2006.01)
*A61F 13/53* (2006.01)

(56) References Cited

U.S. PATENT DOCUMENTS

| | | | |
|---|---|---|---|
| 5,437,653 A * | 8/1995 | Gilman et al. | 604/378 |
| 5,609,588 A * | 3/1997 | DiPalma et al. | 604/378 |
| 5,810,798 A * | 9/1998 | Finch et al. | 604/378 |
| 5,827,254 A * | 10/1998 | Trombetta et al. | 604/378 |
| 5,957,906 A | 9/1999 | Roe et al. | |
| 5,961,505 A * | 10/1999 | Coe et al. | 604/378 |
| 6,232,521 B1 | 5/2001 | Bewick-Sonntag et al. | |
| 6,241,714 B1 | 6/2001 | Raidel et al. | |
| 6,455,753 B1 * | 9/2002 | Glaug et al. | 604/383 |
| 6,492,574 B1 * | 12/2002 | Bednarz et al. | 604/378 |
| 6,498,283 B1 * | 12/2002 | Wada et al. | 604/378 |
| 7,429,689 B2 * | 9/2008 | Chen et al. | 604/378 |
| 7,850,672 B2 * | 12/2010 | Guidotti | A61F 13/15203 604/358 |
| 8,134,043 B2 * | 3/2012 | Di Girolamo et al. | 604/380 |
| 2004/0102124 A1 | 5/2004 | Suzuki | |
| 2005/0267429 A1 | 12/2005 | Cohen | |
| 2010/0291343 A1 | 11/2010 | Bocchio | |

FOREIGN PATENT DOCUMENTS

| | | |
|---|---|---|
| EP | 1374817 A1 | 1/2004 |
| EP | 1403037 A1 | 3/2004 |
| EP | 2184042 A2 | 5/2010 |
| EP | 2298258 A1 | 3/2011 |
| FR | 2011554 A1 | 3/1970 |
| FR | 2044554 A5 | 2/1971 |
| JP | H01-97202 | 4/1989 |
| JP | 2000-507126 | 6/2000 |
| JP | 2002-3235799 A | 11/2002 |
| JP | 2006-014792 A | 1/2006 |
| JP | 2008-284190 A | 11/2008 |
| TW | 201002280 A | 1/2010 |
| WO | WO-97/34559 A1 | 9/1997 |
| WO | WO-97/47263 A1 | 12/1997 |
| WO | WO-00/19955 A2 | 4/2000 |
| WO | WO-00/59431 A1 | 10/2000 |
| WO | WO-01/72251 A1 | 10/2001 |
| WO | WO-02/24133 A1 | 3/2002 |
| WO | WO-2004/084784 A1 | 10/2004 |
| WO | WO-2005/079542 A2 | 9/2005 |
| WO | WO-2005/084596 A1 | 9/2005 |
| WO | WO-2009/005431 A1 | 1/2009 |
| WO | WO-2009/105000 A1 | 8/2009 |

OTHER PUBLICATIONS

Search Report issued in European Patent Application No. 11868516.3 on Dec. 8, 2014 (5 pages).
Decision on Grant dated Jul. 13, 2015 issued in corresponding Russian patent application No. 2014102597 (9 pages) with English-language translation (6 pages).
English translation of a Taiwanese Office Action dated Oct. 7, 2015 issued in corresponding Taiwan patent application No. 101120885 (1 page).

* cited by examiner

ABSORBENT ARTICLE HAVING INTAKE STRUCTURE

CROSS-REFERENCE TO PRIOR APPLICATION

This application is a §371 National Stage application of PCT International Application No. PCT/SE2011/050859 filed Jun. 28, 2011, which is incorporated herein in its entirety.

TECHNICAL FIELD

The disclosure pertains to an absorbent article including a fluid permeable topsheet, a fluid impermeable backsheet and an absorbent core enclosed between the topsheet and the backsheet, the absorbent core including a first absorbent layer and including an opening extending through the first absorbent layer.

BACKGROUND

Absorbent articles of the kind that is worn inside ordinary underpants include incontinence shields and sanitary napkins. As these articles have to be sized and configured to fit in the limited space available in the crotch portion of the underwear, the articles are by necessity designed with a relatively small width. For this reason, a particular problem with such articles is that they may leak at the side edges, before the full absorption capacity of the article has been utilized.

Side leakage may occur as a consequence of absorbed fluid being dispersed equally fast in all directions from the point where the fluid enters the article. This will lead to the fluid escaping the article at the side edges before being distributed to the end portions of the article. Another cause of side leakage may be when the intake capacity of the article is insufficient to allow all fluid that is exuded onto the article to directly enter inside the article. Instead, the fluid will flow on the topsheet and out over the side edges of the article where it can leak out and soil the wearer's clothing. A further drawback when fluid flows on the outside of the topsheet is that a large portion of the body-contacting topsheet will be wet. This is of course highly undesirable as it makes the article unhygienic and unpleasant to wear.

Incontinence shields and sanitary napkins are designed to have a total absorption capacity that is large enough to absorb all fluid that is expected to be released to the absorbent article during a period of wear. However, the fluid is normally not exuded in a steady flow but as sudden gushes of relatively large volume under high pressure and during a very short time period. Accordingly, it would be desirable if the absorbent article was able to receive and contain the emitted fluid with corresponding speed.

Great efforts have been made in the past in order to overcome the side leakage problem in relation to disposable absorbent articles such as incontinence shields and sanitary napkins. However, to date no such effort has been completely successful.

International publication WO 2009/105000 discloses a laminate fibrous web having recesses with a diminishing cross-sectional area in a thickness direction of the web. The web can be used as a fluid intake material and is taught to improve fluid flow through the web.

Although the prior art laminate material may alleviate the side leakage problem to some extent, there is still a great need for further improvements of the side leakage security for the kind of absorbent article that is worn in the crotch portion of an undergarment.

SUMMARY

It is desired to provide an absorbent article having improved intake capacity, fluid distribution properties and leakage security.

In a first aspect, an absorbent article is provided having a longitudinal direction and a transverse direction, side edges extending in the longitudinal direction and end edges extending in the transverse direction and including a fluid permeable topsheet, a fluid impermeable backsheet and an absorbent core enclosed between the topsheet and the backsheet. The absorbent core includes a first absorbent layer, and the first absorbent layer has an opening extending therethrough. A fluid flow control structure is arranged between the first absorbent layer and the backsheet, the fluid flow control structure being a layered structure including a non-perforated fibrous polymeric layer and a first perforated polymeric layer, the first perforated polymeric layer having a basis weight of from 50 g/m$^2$ to 150 g/m$^2$, or a basis weight of from 60 g/m$^2$ to 100 g/m$^2$.

The fluid flow control structure provides the article with high intake capacity.

Moreover, the article in accordance with the first aspect can provide a large void volume for temporary storage of fluid. The void volume is created both by the hollow space or well formed at the opening in the absorbent layer and internally in the porous fluid flow control structure. As soon as the fluid has entered into the fluid flow control structure it may run in the open pore structure of the non-perforated layer and be distributed away from the initially wetted area of the absorbent article. The fluid flow control structure not only enhances fluid transport away from the initially wetted area but also promotes fluid distribution throughout the absorbent core both in the length direction and in the thickness direction of the article. The width of the fluid flow control structure may be smaller than the width of the first absorbent layer, whereby the fluid dispersion rate changes at the edge of the fluid flow control structure. In particular embodiments, the fluid flow control structure is a highly porous structure with less resistance to fluid flow than the first absorbent layer, implying that fluid will by preference continue to move in the fluid flow control structure. Accordingly, the edges of the fluid flow control structure may act as barriers to fluid distribution transversely to the side edges of the absorbent article, reducing the risk of side failure.

In particular embodiments, the opening through the first absorbent layer is placed in the wetting area of the article. The wetting area of the article is that part of the article which is designed to be initially wetted by emitted fluid when the article is being worn and is located in a crotch area of the absorbent article. By arranging the opening in the first absorbent layer in the wetting area, emitted fluid can flow directly into the opening and be collected and temporarily contained in the space defined by the opening and adjacent layers of the absorbent article.

The first absorbent layer in an absorbent article may have one or more openings. The opening or openings may be of any suitable shape or combination of shapes, such as circular, oval, rectangular, square, star-shaped, flower-shaped, heart-shaped, H-shaped, T-shaped, I-shaped etc. Accordingly, the positioning, shape and size of the opening or openings may be varied within the scope of the invention.

Due to its high basis weight and the combination of a perforated layer and a non-perforated layer, the fluid flow control structure will preferably have relatively high bending stiffness. A high bending stiffness provides the absorbent article with an improved ability of resisting transverse compression between the thighs of a wearer of the article and counteracts unwanted deformation of the article during wear, such that the opening in the first absorbent layer is kept open for fluid reception throughout use of the article. The bending stiffness or flexure resistance of the laminate material in the fluid flow control structure may be 0.5-5 N, or 1-4 N, as measured by the modified ASTM D 4032-82 CIRCULAR BEND PROCEDURE. It may be desirable that the bending stiffness of any part of the absorbent article extending laterally outside of the fluid flow control structure has a lower bending stiffness than the fluid flow control structure whereby such less stiff lateral portions of the absorbent article may act as cushioning means between the fluid flow control structure and the wearer's legs.

The absorbent article may include a second absorbent layer being arranged between the fluid flow control structure and the backsheet.

The first perforated polymeric layer may be a nonwoven, a film or a film/nonwoven laminate. In certain embodiments, the first perforated polymeric layer is a nonwoven material. Suitable polymers for the first perforated polymeric layer may be polyolefins, polyesters, polyamides and blends and combinations of such polymers with polypropylene being an exemplary polyolefin. The nonwoven materials may be carded resin bonded materials, carded through-air bonded materials, spunbond-meltbond-spunbond (SMS) materials, carded hydroentangled materials or carded thermobonded materials.

The first perforated polymeric layer may be a three-dimensionally formed layer having penetrating apertures, the apertures extending from a first surface of the layer towards a second surface of the layer, forming protrusions on the second surface and, in particular embodiments, the apertures are funnel-shaped. With a funnel-shaped aperture as used herein is implied an aperture having a tapering shape in its direction of extension such that the cross-sectional area of the aperture is diminishing when moving along the aperture.

The first perforated polymeric layer may be arranged with the second surface facing the non-perforated fibrous polymeric layer or may be arranged with the second surface facing away from the non-perforated fibrous polymeric layer.

The first perforated polymeric layer may be arranged as the first layer of the fluid flow control structure, i.e. as the layer of the structure that is located closest to the topsheet.

The apertures in the first perforated polymeric layer may have an average size of 0.5-5 mm, measured at the smallest diameter of the apertures.

The open area of the first perforated polymeric layer may be 5-30%, or 10-25%.

The non-perforated fibrous polymeric layer may be a high loft material of 20-120 gsm, or 60-100 gsm. The polymer for the non-perforated fibrous polymeric layer may be polyester.

The fluid flow control structure may be a three-layer structure including the non-perforated fibrous polymeric layer, the first perforated polymeric layer and a second perforated polymeric layer, the non-perforated fibrous polymeric layer being sandwiched between the first perforated polymeric layer and the second perforated polymeric layer.

The second perforated polymeric layer may be a three-dimensionally formed layer having apertures extending from a first surface of the web towards a second surface of the web and forming protrusions on the second surface.

The layers in the fluid flow control structure may be attached to each other by means of an adhesive. However, other means of joining of the layers such as thermobonding by hot embossing or ultrasonic bonding may be used as well as layers being joined without using any bonding means. The fluid flow control structure has an overall planar shape. In particular embodiments, the non-perforated fibrous polymer layer has uniform thickness and a uniform pore structure. In further embodiments, bonding between the layers is carried out so as to have minimum impact on the shape and pore structure of the non-perforated fibrous polymer layer.

The polymer materials of the fluid flow control structure may be non-absorbent materials which do not retain any fluid in the material itself. The function of the fluid flow control structure is to provide the absorbent article with temporary fluid holding capacity and to distribute fluid in the article. As the polymer materials in the fluid flow control structure may be hydrophobic, and may have a wetting angle (θ) of 90° or close to 90° implying that they have no or very low wettability when contacted with aqueous fluids, it is may be an advantage if the components of the fluid flow control structure have been treated to lower the wetting angle and render them hydrophilic, i.e. wettable by body fluids. A perfectly wettable material has a wetting angle (θ) of 0°. Any commonly known method for rendering a hydrophobic material hydrophilic may be used, such as treatment with surfactants, plasma or corona treatment, etc.

One aspect of an example embodiment concerns a three-layer fluid flow control structure, wherein both the first perforated polymeric layer and the second perforated polymeric layer may be a three-dimensionally formed layer having penetrating, including, for example, funnel-shaped apertures, extending from a first surface of the layer towards a second surface of the layer and forming protrusions on the second surface. Both perforated polymeric layers may be arranged with the second surface facing the non-perforated fibrous polymeric layer arranged between the perforated polymeric layers.

The apertures in the first and second perforated polymeric layers may be out of register with each other. When the apertures in the first and second perforated polymeric layers are out of register with each other, fluid impinging one of the layers cannot pass directly through the thickness of the fluid flow control structure but is forced to take a more tortuous path through the fluid flow control structure. Moreover, when fluid enters the fluid flow control structure through a first perforated polymeric layer that is arranged facing the topsheet of the article at least some of the fluid travels downward towards the backsheet. When the fluid reaches the second perforated polymeric layer at a non-perforated location, the fluid will run along the second perforated polymeric layer and be distributed inside the fluid flow control structure until it eventually may escape through an aperture in the second perforated polymeric layer. The second perforated polymeric layer may be a three-dimensionally shaped material with apertures forming protrusions on the side of the second perforated polymeric layer that is facing the non-perforated fibrous polymer layer of the fluid flow control structure. In such case, a network of interconnected channels is formed between the protrusions in which network the fluid may be captured and may flow a long distance away from the initially wetted area before leaving the fluid flow control structure.

Three-dimensionally shaped first and second perforated polymeric layers may be oriented with the apexes of the apertures, i.e. the protrusions, directed towards the non-perforated fibrous polymer layer or away from the non-perforated fibrous polymer layer. The three-dimensionally shaped first and second perforated polymeric layers and the high-loft non-perforated fibrous polymeric layer together contribute to the void volume of the fluid flow control structure and to the ability of the structure to contain and move fluid therethrough.

When the fluid flow control structure is a three-layer structure including a non-perforated fibrous polymeric layer that is sandwiched between a first perforated polymeric layer and a second perforated polymeric layer, the second perforated polymeric layer may be different from the first perforated polymeric layer with regard to chemical composition, physical composition, three-dimensionality, open area, aperture size etc. Alternatively, the second perforated polymeric layer may be identical to the first perforated polymeric layer. The second perforated polymeric layer may thus have a basis weight, open area and aperture size corresponding to the first perforated polymeric layer.

Both perforated polymeric layers may be three-dimensionally formed layers as disclosed herein. Each layer may have penetrating apertures that originate in a first surface of the layer and extend towards a second surface of the layer, with the apexes of the apertures forming protrusions at the second surface of the layer. The apertures may be tubular structures, including, for example, funnel-shaped with a diminishing cross-sectional area when moving in a direction from the first surface to the second surface of the perforated layer.

Alternatively, one or both perforated polymer layers may be two-dimensional layers. When at least one of the perforated polymer layers is a three-dimensionally formed layer, such three-dimensionally formed perforated layer may be arranged with the first surface facing away from the non-perforated polymeric layer or with the first surface facing towards the non-perforated polymeric layer. In an absorbent article according to an embodiment of the invention, a three-dimensionally formed perforated polymer layer being oriented with the protrusions facing towards the topsheet of the article will generally promote fluid distribution in the X-Y plane, i.e. in the longitudinal and transverse directions of the article, to a higher extent than a three-dimensionally formed perforated polymer layer being oriented with the protrusions facing towards the backsheet of the article which will generally promote fluid transport in the Z-direction of the article, i.e. in the thickness direction.

The first and second perforated polymeric layers may pass fluid therethrough but act as protective barriers that prevent particles and fibres from entering the fluid flow control structure and interfering with fluid transport inside the fluid flow control structure. The particles and fibres may be absorbent materials from such as absorbent polymer particles commonly known as "superabsorbents", cellulose fluff pulp fibres, etc.

The fluid flow control structure may have a high resistance to compression as measured in the Compression Test disclosed herein. Accordingly, the thickness of the flow control structure at 5 kPa may be 60-80% of the thickness at 0.5 KPa at a first, second and third compression performed according to the compression test disclosed herein.

In an absorbent article according to an embodiment of the invention, the first absorbent layer may have more than one opening extending therethrough. The openings may be placed in the same general area of the absorbent article, such as in a crotch portion of the article or may be placed in different portions of the article such as in two or more of the crotch portion and the end portions. The crotch portion, as used herein, is the portion of the article that is designed to be placed in the crotch of a wearer and to be in contact with the pudendal area of the wearer. The crotch portion includes the wetting area of the article and can be asymmetrically placed in the longitudinal direction of the article. The end portions are placed on either side of the crotch portion in the longitudinal direction of the article. The article may be designed with end portions that are specifically adapted to be placed towards the front or the rear of a wearer and may then differ in size, shape, etc. to allow a user to apply the article in a correct way inside the underwear.

The absorbent article may be provided with means for fastening of the article in ordinary underwear or other supporting pant-garment. The fastening means may be adhesive fasteners, frictional fasteners, mechanical fasteners such as the hook part of a hook-and-loop fastener or combinations of different types of fasteners, as known in the art.

The absorbent article may be a diaper of the open type that is fastened around the lower torso of a wearer by means of tape fasteners, belts or similar or may be a closed-type pant diaper. The absorbent article may alternatively be of a kind that is worn inside a supporting panty or with a holder, such as a sanitary napkin, a panty liner or an incontinence protector. In certain embodiments, the absorbent article is an incontinence protector.

An absorbent article may comprise a fluid permeable topsheet, disposed at the surface of the incontinence protector which is intended to be facing a wearer of the incontinence protector, a backsheet disposed at the surface of the incontinence protector that is intended to be facing the undergarment of the wearer, and an absorbent core, enclosed between the topsheet and the backsheet.

The covering may be of a kind where the topsheet and the backsheet of the incontinence protector extend together laterally outside of the absorbent core along the whole circumference of the absorbent core and are connected to each other in an edge join around the periphery of the absorbent core. An edge join may be formed in any suitable manner as known in the art such as by means of adhesive, ultrasonic bonding, thermobonding, stitching, etc. Alternative covering arrangements such as wrapped-around covers are also conceivable within the scope of the invention.

The topsheet may include any material which is suitable for the purpose. Examples of commonly found topsheet materials are nonwoven materials, perforated plastic films, plastic or textile mesh, and fluid permeable foam layers. Laminates include two or more topsheet materials are also commonly employed, as are topsheets including different materials within different parts of the fluid permeable wearer-facing surface. In certain embodiments, the topsheet is a non-apertured nonwoven web.

The backsheet is preferably fluid impermeable. However, backsheet materials that are only resistant to fluid penetration may be used particularly in instances where relatively small amounts of urine are expected to be taken up by the incontinence protector. The backsheet may be a thin, flexible, fluid-impermeable plastic film, but fluid-impermeable nonwoven materials, fluid impermeable foams and fluid impermeable laminates are also contemplated within the scope of the invention. The backsheet may be breathable, implying that air and vapor may pass through the backsheet. Furthermore, the backsheet may have an outer, garment-facing surface of a textile material such as nonwoven.

The absorbent core may be made up of any suitable absorbent or fluid uptake material as known in the art, such as one or more layers of cellulose fluff pulp, foam, fiber waddings, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The absorbent core may further incorporate components for improving the properties of the absorbent core. Some examples of such components are binder fibers, fluid-dispersing materials, fluid acquisition materials, etc. as known in the art.

The absorbent article may include more than one absorbent core. The cores may be an upper larger core and a lower, smaller core.

The article may further include components such as elastic elements. The elastic elements may be arranged along the side edges of the absorbent article. Elastic elements arranged along the side edges of the absorbent article improve the anatomical fit of the article by inducing longitudinal bending of the article in conformation with the curvature in a wearer's crotch.

When the absorbent core includes a first absorbent layer and a second absorbent layer the fluid flow control structure may be arranged between the first absorbent layer and the second absorbent layer. The first absorbent layer may be placed beneath and in direct contact with the topsheet. Alternatively, the first absorbent layer may be placed in indirect contact with the topsheet through one or more intervening components such as tissue layers, acquisition layers or further absorbent layers. Similarly, the second absorbent layer may be placed directly beneath the fluid flow control structure and in direct contact with the fluid flow control structure and the backsheet but may alternatively be in indirect contact with one or both of those components by intervening components.

The absorbent layers of the core may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may include a mixture of absorbent and/or non-absorbent fibres and superabsorbent material, wherein the ratio of superabsorbent material to fibres may vary in the layer.

The fluid flow control structure may be of rectangular shape and may be surrounded in the longitudinal and lateral directions by portions of the absorbent core. Although other shapes and configurations for the fluid flow control structure may be used, it is generally advantageous if the fluid flow control structure has the same or smaller width than the absorbent core and also the same or shorter length than the absorbent core. The fluid flow control structure has a highly porous internal structure with less resistance to fluid flow than conventional absorption materials. This means that the fluid dispersion rate changes at the edge of the fluid flow control structure so that fluid reaching the edge will continue to move primarily in the fluid flow control structure where the flow resistance is low before being absorbed by the core material. In this way, the edges of the fluid flow control structure act as barriers to fluid distribution transversely to the side edges of the absorbent article, thus reducing the risk of side failure. Conventional absorption materials such as cellulose fluff pulp, and superabsorbents have comparatively smaller capillaries than the fluid flow control structure. A fibrous structure with fine capillaries has a low fluid uptake capacity, but high fluid retention capability once the fluid has entered the structure. A superabsorbent material has even lower uptake rate and higher retention capability than the fibrous absorbent structures due to fluid uptake in such materials being driven mainly by osmotic pressure.

The components in the absorbent article may be connected to each other by conventional means such as construction adhesive, heat bonding, ultrasonic bonding, etc. It may not be necessary to bond internal components of the absorbent article to each other by special bonding means. Accordingly, it may suffice that such components are held together by frictional forces.

Test Methods

The modified ASTM D 4032-82 CIRCULAR BEND PROCEDURE

Apparatus:

The apparatus is a modified Circular Bend Stiffness Tester, having the following parts:

A smooth-polished steel plate platform which is 102.0× 102.0×6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle point extending 0.88 millimeter therefrom having a 0.33 millimeter base diameter and a point having a radius of less than 0.5 millimeter, the plunger being mounted concentric with the orifice and having equal clearance on all sides. Note that the needle point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force-measurement gauge and more specifically an Instron inverted compression load cell. The load cell has a load range of from 0.0 to 10 N.

An actuator, and more specifically an Instron™ tester having an inverted compression load cell. The Instron™ tester is made by the Instron Engineering Corporation, Canton, Mass.

Number and Preparation of Specimens:

In order to perform the procedure for this test, 10 test specimens of 37.5×37.5 millimeter are cut from the tested laminate material.

Procedure:

The procedure for the CIRCULAR BEND PROCEDURE is as follows. The specimens are conditioned by leaving them in a room which is 21±1° and 50±2% relative humidity for a period of two hours. The test plate is leveled. The plunger speed is set at 50.0 centimeters per minute per full stroke length. A specimen is centered on the orifice platform below the plunger such that the body surface of the specimen is facing the plunger and the garment surface is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Compressibility

Procedure:

The principle of the method is to slowly compress a material with a metal rod to a force of 5 N while continuously measuring the thickness of the material. The result includes the data points for force and extension. The force translates to a pressure given the contact area of the rod. The metal rod is cylindrical and has a diameter of 10 mm with a flat base. The rod is mounted in a 10N load cell in the upper fixture of an Instron testing apparatus. A flat plate is mounted in the bottom fixture and is centered under the rod so that a sample may be placed on top of the plate and be compressed without movement of the plate. The rate of movement of the rod is 5 mm per minute. These settings have been pre-programmed into an Instron Bluehill program called "New Mecano 5 N", but before running a test, the program settings should be checked in order to make sure that all limits are set to their proper values. Running with a modified version could lead to damage to the equipment, especially the sensitive load cell.

Running a Test:

The first run is an empty run without a sample. This run is used to find the zero thickness position, which is where the steel plate stops the rod. The empty run typically generates forces higher than the maximum limit set before the rod stops, because of the rapid increase in force that occurs when the rod impacts the metal and for which the apparatus cannot compensate sufficiently quickly. Care should be taken to ascertain that the load cell can withstand the impact without being damaged. Special settings can be used for the empty run to lower the limiting maximum force and the speed of the rod.

When the rod stops, the Instron equipment awaits user input. The extension is then manually reset to zero. This ensures that the extension is set to zero at the exact correct point where the rod touches the base and the extension is measured relative to the bottom plate. The rod may thereafter be manually moved up so that a sample can be placed on the lower plate.

To test a sample, the rod is moved manually so that it is above the surface of the sample and the program is started. The rod moves down at a speed of 5 mm per minute until the limiting force is reached.

Samples:

The samples are squares with 50 millimeter sides punched from the tested material. If the material has varying thickness, the samples are taken from the thickest parts of the material. The rod is pressed into the centre of the sample and each sample is tested three times without being moved between runs. Ten samples of each tested material are used, giving thirty measurements in total.

Results:

The result is the complete set of data points for force versus extension. The force is typically recalculated into pressure using the force measured divided by the bottom area of the rod. The result may be plotted and reported or a specific pressure may be chosen and the thickness noted, so that the result is a thickness for a given pressure.

Open Area and Hole Diameter Measurement

The following method may be used to determine the open area and hole diameter for an apertured material:

Apparatus:
  a Nikon microscope
  a personal computer
  software NIS-Elements BR 3.10

Procedure:
  collect a sample of the apertured material
  position the sample on the reading surface of the microscope
  start the software
  catch a representative image of the sample
  perform the analysis of the properties by contrast technique involving highlighting of the areas occupied by the holes.

The software calculates the diameters of the highlighted holes as major diagonal and minor diagonal of a rhombus inscribed in the hole. The ratio between the diameters is used to determine the actual average conformation of the holes to a circular shape, wherein a ratio of 1 implies a perfectly circular shape.

The average hole area value obtained by means of the software is used to calculate the percent open area.

Alternative methods for determining open area and hole diameter may be used, such as manual methods and methods based on scanning electron microscopy.

BRIEF DESCRIPTION OF THE DRAWINGS

Embodiments of the invention will be described in greater detail below with reference to the figures shown in the appended drawings.

DESCRIPTION OF EMBODIMENTS

Figure 1:
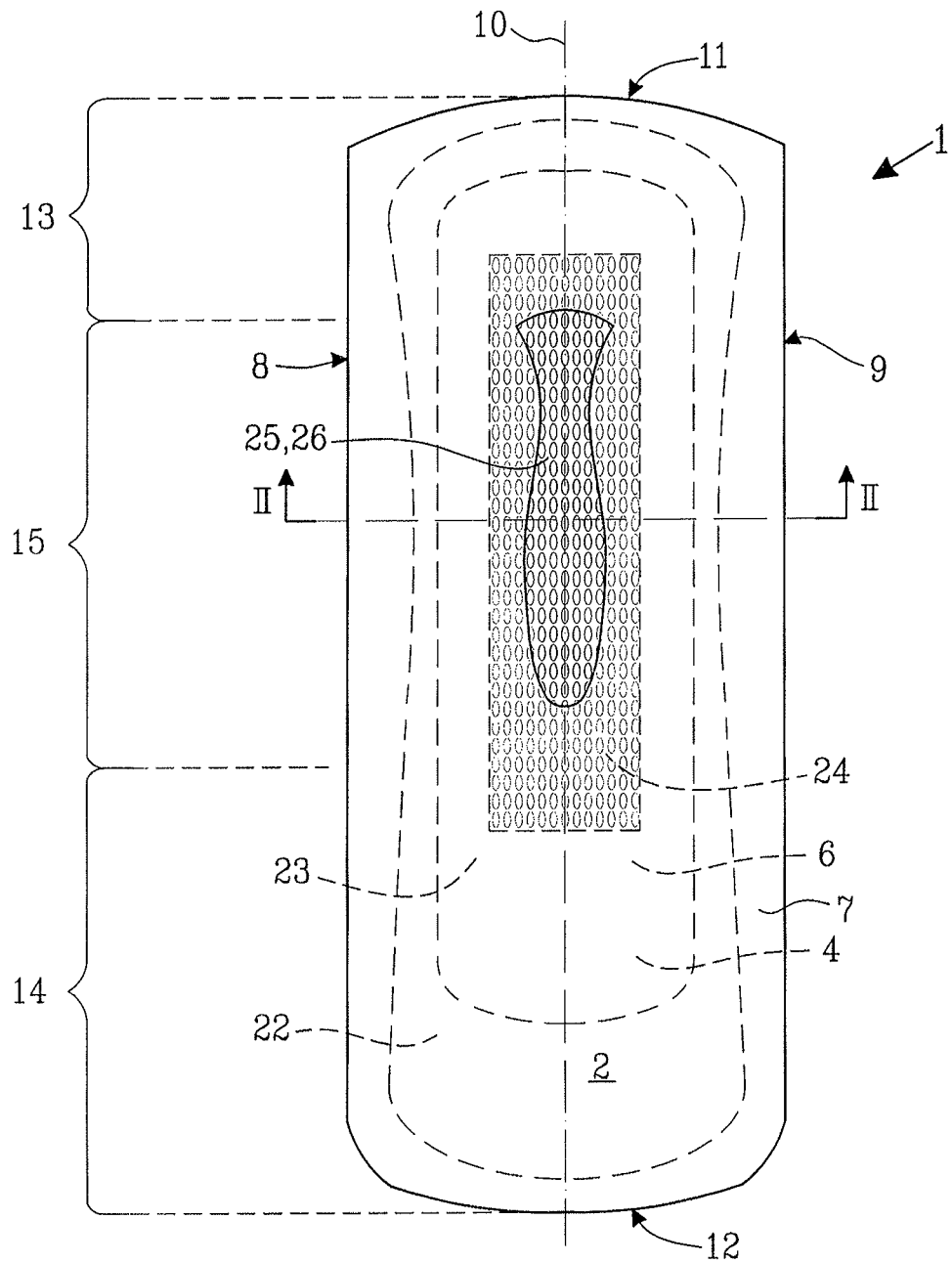
FIG. 1 shows an incontinence protector according to an embodiment of the invention, seen from the side which will be facing the undergarment when the incontinence protector is being worn.
Figure 2:
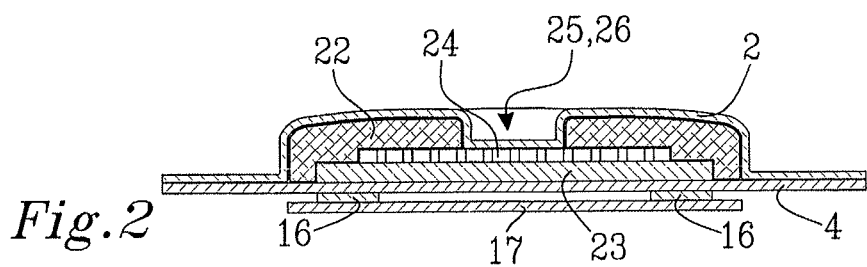
FIG. 2 shows a cross-section through the incontinence protector in FIG. 1, taken along the line II-II.

The absorbent article is exemplified by an incontinence protector as shown in FIGS. 1 and 2. It is to be understood that the invention is equally applicable to any type of hygienic absorbent article. Such articles include incontinence protectors, sanitary napkins, panty liners, diapers with tape fasteners, pant diapers or belted diapers.

FIG. 1 shows a urine incontinence protector 1 seen from the side of the incontinence protector 1 that is intended to be facing towards a wearer's body when the incontinence protector 1 is being worn.

The incontinence protector 1 includes a fluid permeable topsheet 2, a backsheet 4 and an absorbent core 6, enclosed between the topsheet 2 and the backsheet 4.

The topsheet 2 and the backsheet 4 of the incontinence protector 1 are shown to extend together laterally outside of the absorbent core 6 along the whole circumference of the absorbent core 6 and are connected to each other in an edge join 7 around the periphery of the absorbent core 6.

The topsheet 2 and the backsheet 4 may include any material suitable for the particular purpose, as disclosed herein.

The incontinence protector 1 as shown in FIGS. 1 and 2 has elongate, generally rectangular shape when fully extended in all directions. The word "generally" in this context means that, for instance, the corners of the incontinence protector 1 may be rounded, or that the edges of the incontinence protector 1 may not be completely linear as is illustrated in FIG. 1. The shape of the incontinence protector 1 shown in FIG. 1 should not be considered limiting to the invention. Accordingly, any other suitable shape may be used, such as hourglass shape, trapezoidal shape, triangular shape an oval shape, etc. The shape of the article may be symmetrical about a transverse centre line through the article, as shown in FIG. 1 or may be asymmetrical with end portions having differing shapes and/or differing sizes.

The incontinence protector 1 in FIGS. 1 and 2 has two longitudinal side edges 8, 9 having equal length and extending generally in the same direction as a longitudinal center line 10 through the incontinence protector 1. Front and rear end edges 11, 12 extend transversely to the longitudinal center line 10 at the ends of the incontinence protector. The rear end edge 12 is intended to be orientated rearwards during use of the incontinence protector 1, and the front end edge 11 is intended to be facing forwards towards the abdomen of the wearer.

The incontinence protector 1 has a front end portion 13, a rear end portion 14 and a crotch portion 15 located intermediate the end portions 13,14. The crotch portion 15 is that portion of the incontinence protector 1 which is intended to be placed against the crotch of a wearer during wearing of the protector 1 and to constitute the main acquisition area for body fluid that reaches the protector 1.

The incontinence protector 1 further has fastening means 16 for fastening of the incontinence protector 1 inside a supporting pant garment, such as a pair of underpants. The fastening means 16 is in the form of two longitudinally extending bands of pressure sensitive adhesive arranged on the garment-facing surface of the backsheet 4. In FIG. 2, the fastening means 16 is shown to be covered by a releasable protective layer 17. The protective layer may be a siliconized paper, a nonwoven or any other releasable material as is known in the art. Before placing the incontinence protector in the supporting pant garment, the protective layer is removed from the fastening means 16 to expose the adhesive and make it available for fastening to the pant garment.

The fastening means 16 is optional to the invention and may be omitted, if desired. When using an adhesive fastening means, any suitable adhesive pattern may be used such as full coating of the backsheet, one or more longitudinal adhesive band, transverse bands, dots, circles, curves, stars, etc. Furthermore, the fastening means 16 may be a mechanical fastener such as hook-type fasteners, clips, press studs, etc. or may be a frictional fastener such as a frictional coating or open-celled foam. Combinations of different types of fasteners are also conceivable.

The absorbent core 6 of the incontinence protector 1 shown in FIGS. 1 and 2 includes a first absorbent layer 22 and a second absorbent layer 23. A fluid flow control structure 24 is arranged between the first absorbent layer 22 and the second absorbent layer 23. In the incontinence protector 1 in FIGS. 1 and 2, the first absorbent layer 22 is placed beneath and in direct contact with the topsheet 2. Alternative arrangements may be used, as disclosed herein.

The first absorbent layer 22 and the second absorbent layer 23 are shown to have generally rectangular shapes. The second absorbent layer 23 is placed beneath the first absorbent layer 22. The second absorbent layer 23 is somewhat smaller than the first absorbent layer 22 so that the first absorbent layer 22 extends beyond the second absorbent layer 23 forward and rearward in the incontinence protector 1. The size and shape of the absorbent layers may be different from those shown in the figures without departing from the invention. Moreover, the second absorbent layer 23 may be omitted in the absorbent article or the article may include one or more further absorbent layers.

The first absorbent layer 22 has an opening 25 extending completely through the layer 22 in the crotch portion 15 of the incontinence protector 1. The opening 25 has elongate shape. Without departing from the invention, the shape, size and location of the opening 25 in the first absorbent layer 22 may be different from what is shown in FIG. 1, as described herein.

The topsheet 2 is shown to extend down into the cavity 26 that is defined by the opening 25 in the first absorbent layer 22 and the topsheet-facing surface of the fluid flow control structure 24. The cavity 26 is located in the wetting area of the incontinence protector 1 and will in use be placed directly beneath the urethra and the vaginal opening of a female wearer. Any body fluid that is released to the incontinence protector 1 will directly be collected in the cavity 26 and be temporarily contained therein until it is distributed further into and throughout the absorbent core 6.

A portion of the fluid that is collected in the cavity 26 may be absorbed by the first absorbent layer through the walls of the cavity 26. However, the majority of the fluid will continue downward in the incontinence protector 1, through the bottom of the cavity 26 and into the fluid flow control structure 1 where it is distributed longitudinally and laterally along the flow control structure 24, as described in more detail with reference to FIGS. 3 and 4.

The fluid flow control structure 24 is shown in FIG. 1 to be of rectangular shape and to be surrounded in the longitudinal and lateral directions by portions of the absorbent core 6. It is generally advantageous if the fluid flow control structure 24 has smaller width and also is shorter than the absorbent core 6.

The components in the incontinence protector 1 may be connected to each other by conventional means such as construction adhesive, heat bonding, ultrasonic bonding, etc. It may not be necessary to bond internal components of the incontinence protector to each other by special bonding means. Hence, it may suffice that such components are held together by frictional forces.

The function of a fluid flow control structure 24 and its use in an absorbent article such as the incontinence protector 1 in FIGS. 1 and 2 will now be described with reference to FIGS. 3 and 4. The fluid flow control structure 24 in FIGS. 3 and 4 is a three-layer structure including a non-perforated fibrous polymeric layer 31 that is sandwiched between a first perforated polymeric layer 32 and a second perforated polymeric layer 33.

The perforated polymeric layers 32,33 are three-dimensionally formed layers. Each layer 32,33 has penetrating apertures 34 that originate in a first surface 32',33' of the layer and extend towards a second surface 32",33" of the layer, with the apexes of the apertures 34 forming protrusions 35 at the second surface 32",33". The apertures are tubular structures and can be, for example, funnel-shaped, as seen in FIG. 3. The distance between the first surface 32',33' and the second surface 32",33" is the apparent thickness of the respective layers 32,33.

Figure 3:
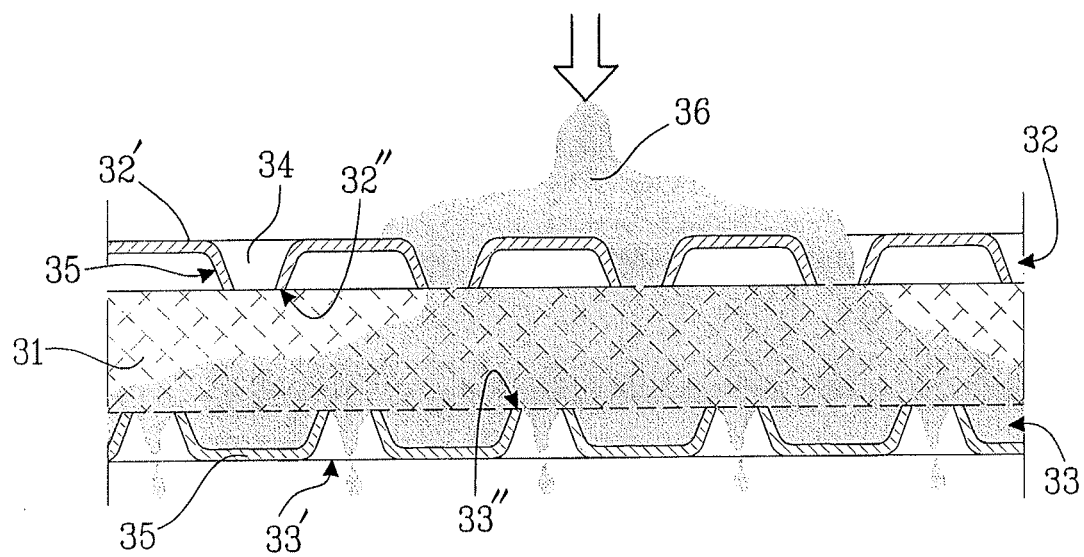
FIG. 3 shows a section through a fluid flow control structure according to an embodiment of the invention.
Figure 4:
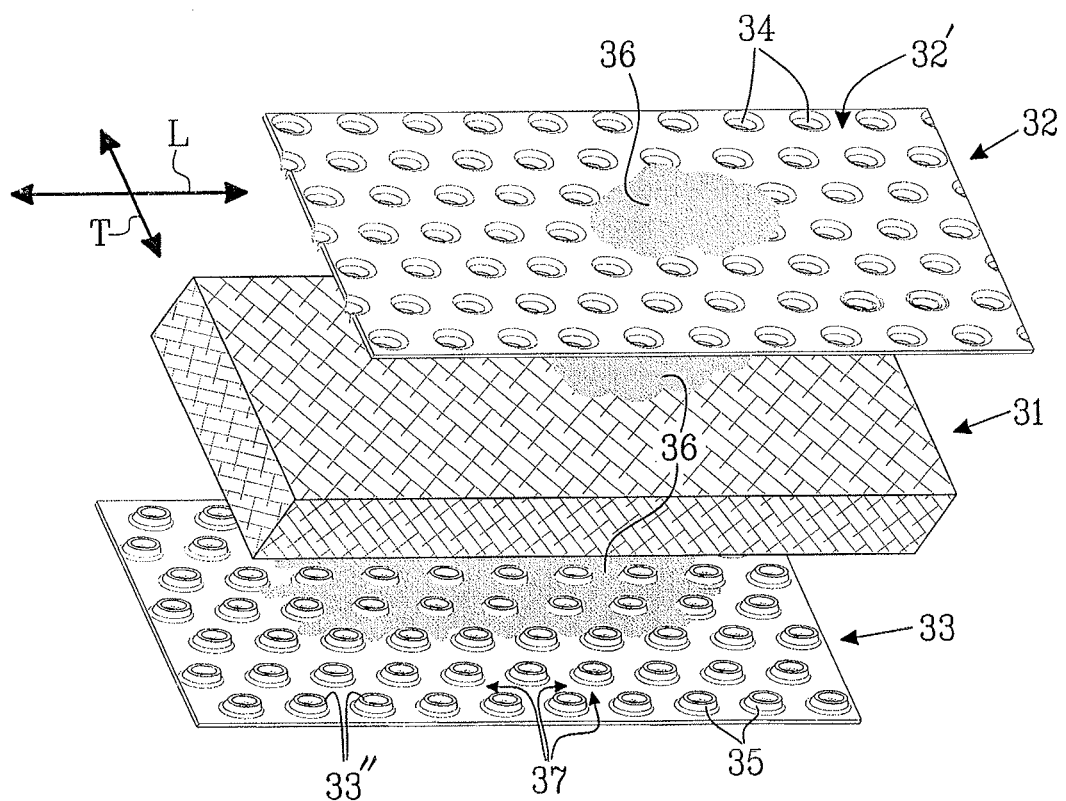
FIG. 4 shows an exploded perspective view of a fluid flow control structure according to an embodiment of the invention.

When fluid 36 reaches the first surface 32' of the first perforated polymeric layer 32, it spreads slightly on the surface 32' before passing through the apertures 34 into the non-perforated fibrous polymeric layer 31, as is shown in FIG. 3. The non-perforated fibrous polymeric layer 31 offers very little resistance to fluid flow, whereby the fluid runs relatively freely in the layer 31 until it is finally moved by gravity down to the second perforated layer 33 where further downward movement is restricted by the second surface 33" of the second perforated layer 33. A small amount of fluid may run out of the fluid flow control structure 24 by entering the openings at the apexes of the protrusions 35 on the second perforated layer 33. However, most of the fluid will spread further on the second surface 33" of the second layer 33 by running in the interconnected channel network 37 that is formed between the protrusions 35, as illustrated in FIG. 4.

The fluid that is captured in the interconnected channel network 37 will generally not exit the fluid flow control structure 24 until it reaches the edges of the fluid flow control structure 24 or when the channel network 37 is saturated with fluid such that the fluid level raises above the height of the protrusions 35. Accordingly, the fluid 36 will be distributed along the second surface 33" in all directions from the initial point of fluid impact. The apertures 34 may be distributed in the perforated polymeric layers 32,33 so that fluid dispersion takes place to a greater degree in a direction corresponding to the longitudinal direction of the absorbent article in which the fluid flow control structure 24 is placed than in a direction transverse thereto. As shown in FIG. 4, the perforated polymeric layers 32,33 have apertures 34 arranged in staggered rows, such that generally linear channels are formed between the apertures 34 in a longitudinal direction L of the layers 32,33 and non-linear channels are formed in the transverse direction T. Such an arrangement of the apertures 34 in the second perforated polymeric layer 33 serves to promote longitudinal fluid flow in the fluid flow control structure and limit transverse fluid flow.

Figure 5A:
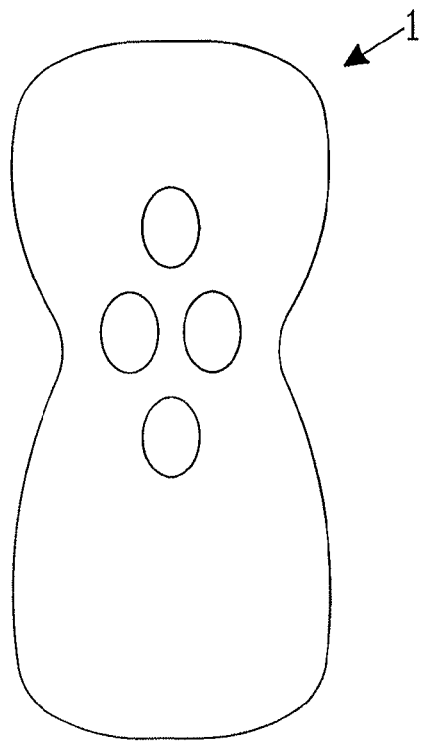
FIGS. 5a-d show absorbent layers having openings therein.
Figure 5B:
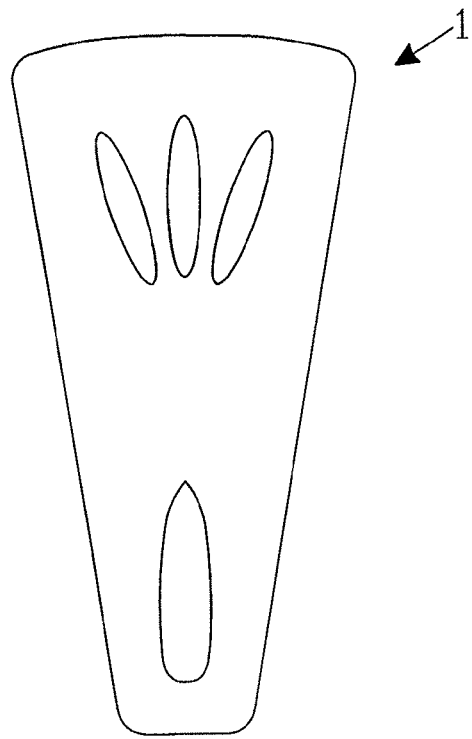
Figure 5C:
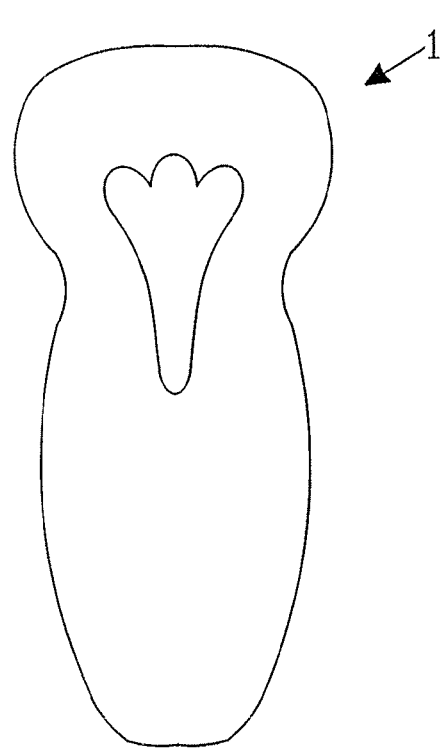
Figure 5D:
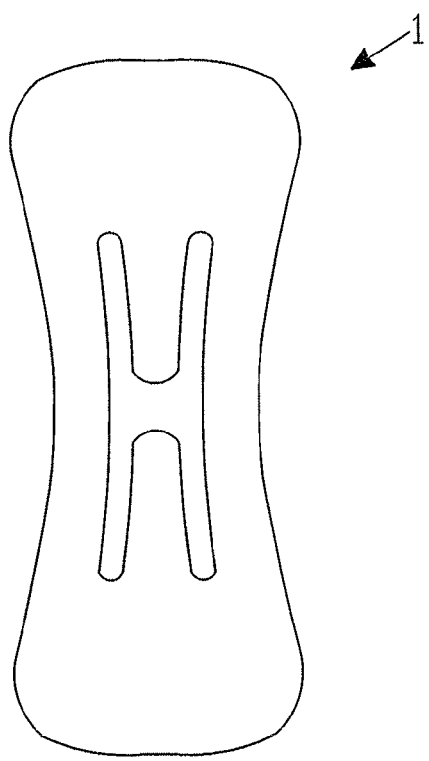

FIGS. 5a-5d illustrate that the first absorbent layer in an absorbent article may have one or more openings of different shapes and configurations. The particular configurations shown in FIGS. 5a-d should not be regarded as limiting to the invention but are only offered as examples of the many variations that are possible within the scope of the invention. FIG. 5a shows a first absorbent layer having multiple circular openings in the crotch portion of the layer. FIG. 5b shows a first absorbent layer having three elongate openings in the front portion of the layer and a single elongate opening in the rear portion of the layer. FIG. 5c shows a first absorbent layer having an opening shaped as a duck's foot and FIG. 5d shows a first absorbent layer having an H-shaped opening. The layer shown in FIG. 5a may, for instance, be suitable when a large total opening area is desired without compromising the wish of having a coherent layer that will not fall apart or otherwise deform during production of the absorbent article. A layer such as shown in FIGS. 5b and 5c and having a large open area positioned to the front, may be particularly useful in sanitary napkins for day-time use. The FIG. 5b layer would additionally work well in absorbent articles intended for night-time use where fluid may run rearward between the wearer's buttocks. The FIG. 5d layer may be particularly suited for incontinence protectors where it may be desired to quickly channel fluid from the crotch portion of the absorbent article towards the ends thereof.

FIGS. 5a-d are also intended to show that the first absorbent layer, as well as the overall absorbent article may have any suitable shape, as known in the art.

The invention claimed is:

1. An absorbent article having a longitudinal direction and a transverse direction, side edges extending in the longitudinal direction and end edges extending in the transverse direction and comprising:
   a fluid permeable topsheet,
   a fluid impermeable backsheet, and
   an absorbent core enclosed between said topsheet and said backsheet, said absorbent core comprising,
      a first absorbent layer having an opening that passes through the first absorbent layer from one major surface to an opposing major surface and therebetween the opening is surrounded by a closed periphery of first absorbent layer,
      a fluid flow control structure, and
      a second absorbent layer arranged between the fluid flow control structure and the fluid impermeable backsheet,
   wherein the fluid flow control structure is arranged between said first absorbent layer and said backsheet, said fluid flow control structure being a layered structure comprising a non-perforated fibrous polymeric layer and a first perforated polymeric layer, and
   wherein the opening extends along a longitudinal center line of the absorbent article, the longitudinal center line being in parallel with the longitudinal direction of the absorbent article, and the fluid permeable top sheet is in direct contact with the fluid flow control structure via the opening.

2. The absorbent article according to claim 1, wherein the first perforated polymeric layer has a basis weight of from 60 g/m² to 100 g/m².

3. The absorbent article according to claim 1, wherein the first perforated polymeric layer is a nonwoven, a film or a film/nonwoven laminate.

4. The absorbent article according to claim 1, wherein the first perforated polymeric layer is a three-dimensionally formed layer having penetrating apertures extending from a first surface of the first perforated polymeric layer towards a second surface of the first perforated polymeric layer and forming protrusions on said second surface.

5. The absorbent article according to claim 4, wherein the first perforated polymeric layer is arranged with said second surface facing the non-perforated fibrous polymeric layer.

6. The absorbent article according to claim 4, wherein the first perforated polymeric layer is arranged with said second surface facing away from the non-perforated fibrous polymeric layer.

7. The absorbent article according to claim 4, wherein the average size of the apertures in the first perforated polymeric layer is 0.5-5 mm.

8. The absorbent article according to claim 1, wherein open areas of the first perforated polymeric layer comprise 5-30% of the first perforated polymeric layer.

9. The absorbent article according to claim 1, wherein said fluid flow control structure is a three-layer structure consisting of the non-perforated fibrous polymeric layer, the first perforated polymeric layer and a second perforated polymeric layer, the non-perforated fibrous polymeric layer being sandwiched between the first perforated polymeric layer and the second perforated polymeric layer.

10. The absorbent article according to claim 9, wherein apertures in the first perforated polymeric layer and the second perforated polymeric layer are out of register with each other.

11. The absorbent article according to claim 9, wherein the second perforated polymeric layer has a basis weight of from 50 g/m² to 150 g/m².

12. The absorbent article according to claim 9, wherein the second perforated polymeric layer is a three-dimensionally formed layer having apertures extending from a first surface of the second perforated polymeric layer towards a second surface of the second perforated polymeric layer and forming protrusions on said second surface of the second perforated polymeric layer.

13. The absorbent article according to claim 12, wherein the second perforated polymeric layer is arranged with said second surface of the second perforated polymeric layer facing the non-perforated fibrous polymeric layer.

14. The absorbent article according to claim 12, wherein the second perforated polymeric layer is arranged with said second surface of the second perforated polymeric layer facing away from the non-perforated fibrous polymeric layer.

15. The absorbent article according to claim 12, wherein the average size of the apertures in the second perforated polymeric layer is 0.5-5 mm.

16. The absorbent article according to claim 9, wherein open areas of the second perforated polymeric layer comprise 5-30% of the second perforated polymeric layer.

17. The absorbent article according to claim 9, wherein the second perforated polymeric layer is a nonwoven, a film or a film/nonwoven laminate.

18. The absorbent article according to claim 1, wherein the thickness of said fluid flow control structure at 5 kPa is 60-80% of the thickness at 0.5 kPa at a first, second and third compression performed according to the compression test disclosed herein.

19. The absorbent article according to claim 1, wherein the bending stiffness of the layered structure in said fluid flow control structure is 0.5-5 N as measured by the modified ASTM D 4032-82 CIRCULAR BEND PROCEDURE.

20. The absorbent article according to claim 1, wherein the basis weight of the non-perforated fibrous polymeric layer is from 20-120 gsm.

21. The absorbent article according to claim 1, wherein the opening extends through an entire crotch portion of the absorbent article.

22. The absorbent article according to claim 1, wherein the fluid permeable topsheet is not perforated.

23. The absorbent article according to claim 1, wherein the polymers in the first perforated polymeric layer are selected from polyolefins, polyesters, polyamides and blends and combinations thereof, and the first perforated polymeric layer has a basis weight from 50 $g/m^2$ to 150 $g/m^2$.

24. The absorbent article according to claim 1, wherein the fluid permeable top sheet is in contact with the first absorbent layer of the absorbent core at an area other than where the opening is located.

25. The absorbent article according to claim 1, wherein the fluid permeable top sheet is in contact with the fluid flow control structure via the opening, such that a cavity is formed along the longitudinal center line of the absorbent article.

* * * * *